United States Patent
Mägerlein et al.

(10) Patent No.: US 7,718,827 B2
(45) Date of Patent: May 18, 2010

(54) PROCESS FOR THE RUTHENIUM-CATALYSED OXIDATION OF ALCOHOLS BY MEANS OF HYPOCHLORITE

(75) Inventors: Wolfgang Mägerlein, Köln (DE); Angela Köckritz, Berlin (DE); Andrea Dittmar, Berlin (DE); Michael Sebek, Berlin (DE)

(73) Assignee: Saltigo GmbH, Langenfeld (DE)

( * ) Notice: Subject to any disclaimer, the term of this patent is extended or adjusted under 35 U.S.C. 154(b) by 0 days.

(21) Appl. No.: 11/476,528

(22) Filed: Jun. 28, 2006

(65) Prior Publication Data

US 2007/0004922 A1  Jan. 4, 2007

(30) Foreign Application Priority Data

Jul. 1, 2005  (DE) .................. 10 2005 030 728

(51) Int. Cl.
*C07C 45/38* (2006.01)
(52) U.S. Cl. ..................................... 568/426; 568/437
(58) Field of Classification Search ................. 568/426, 568/437
See application file for complete search history.

(56) References Cited

U.S. PATENT DOCUMENTS

| 4,647,592 | A |   | 3/1987  | Mauldin |         |
|-----------|---|---|---------|---------|---------|
| 4,960,948 | A | * | 10/1990 | Sanderson et al. | 568/405 |
| 4,980,514 | A | * | 12/1990 | Sanderson et al. | 568/405 |
| 5,856,584 | A | * | 1/1999  | Prakash et al.   | 568/449 |
| 6,573,409 | B1| * | 6/2003  | Ebner et al.     | 568/449 |

FOREIGN PATENT DOCUMENTS

| EP | 1 031 378  | 8/2000  |
| JP | 62 265244  | 11/1987 |

OTHER PUBLICATIONS

Angew. Chem. 2002, 114, 4720-4724 (N. Mizuno et al.).
R. A. Sheldon et al., *Org. Lett.* 2002, 4, 1659.
*Adv. Synth. Catal.* 2003, 345, 1321.
G. Balavoine et al., *J. Mol. Catal.* 1985, 30, 125.
*Tetrahedron Letters* 2000, 41, 3971-3974.
Kockritz, et al., *Journal of Molecular Catalysis* 2006, 85-99.

* cited by examiner

*Primary Examiner*—Sikarl A Witherspoon
(74) *Attorney, Agent, or Firm*—Michael A. Miller

(57) ABSTRACT

The present invention relates to a process for preparing aldehydes or ketones using an alkali metal hypochlorite or an alkaline earth metal hypochlorite in the presence of a ruthenium catalysts.

9 Claims, No Drawings

PROCESS FOR THE RUTHENIUM-CATALYSED OXIDATION OF ALCOHOLS BY MEANS OF HYPOCHLORITE

The present invention relates to a process for preparing aldehydes or ketones using an alkali metal hypochlorite or an alkaline earth metal hypochlorite in the presence of a ruthenium catalysts.

Aldehydes and ketones are important organic products and intermediates in the chemical industry, for example for pharmaceutical and agrochemical active ingredients and for specialty chemicals. A customary method of synthesizing aldehydes or ketones is the oxidation of the corresponding primary or secondary alcohols. Metal-catalysed oxidation reactions in which inexpensive and easy-to-handle oxidants can be used are of particular importance for this purpose in the industry. Compared to methods in which stoichiometric amounts of metal salts, e.g. chromium(VI) compounds, manganese dioxide or permanganate, are used, catalytic processes have considerable ecological and economic advantages. A suitable active metal for catalytic alcohol oxidations is, for example, ruthenium which is significantly less expensive and less toxic than other metals which are likewise suitable as catalyst, e.g. palladium, platinum or osmium.

Angew. Chem. 2002, 114, 4720-4724 (N. Mizuno et al.) describes $Ru/Al_2O_3$ catalysts for the oxidation of primary alcohols to aldehydes by means of molecular oxygen. $RuO_2$, Ru/C, $Ru/CeO_2$, Ru/hydrotalcite and Ru-hydroxyapatite catalysts can also be used in this reaction. However, molecular oxygen has the disadvantage from a safety point of view that it is able to form ignitable or explosive mixtures with other substances.

R. A. Sheldon et al., *Org. Lett.* 2002, 4, 1659, and *Adv. Synth. Catal.* 2003, 345, 1321, and also G. Balavoine et al., *J. Mol. Catal.* 1985, 30, 125, disclose catalyst systems in which Ru compounds such as tetra-n-propylammonium perruthenate (n-$Pr_4NRuO_4$) or $RuCl_2(ligand)_2$, etc., are used in combination with sodium hypochlorite as oxidant. However, these are homogeneous catalyst systems which compared to heterogeneous catalyst systems have the disadvantage that the separation from the products and recycling is more difficult and they often display only low selectivities (cf. *Tetrahedron Letters* 2000, 41, 3971-3974).

*Tetrahedron Letters* 2000, 41, 3971-3974, describes the oxidation of alcohols to aldehydes or ketones using poly(4-vinylpyridine)-supported ruthenium catalysts, with NaOCl, inter alia, being suitable as possible oxidant. However, such polymer-supported catalysts have the disadvantage that the support polymers themselves either have to be prepared before preparation of the catalysts or else, if they are commercially available, they are more expensive than conventional inorganic support materials. Furthermore, such organic, polymeric support materials can lack resistance to oxidants.

There is therefore a continuing need for a catalytic process for the oxidation of alcohols to aldehydes or ketones with high selectivity, which process does not have the abovementioned disadvantages.

It is therefore an object of the present invention to provide a simple process for the catalytic oxidation of alcohols to aldehydes or ketones, in which the desired products are obtained with high selectivity using inexpensive, easy-to-handle oxidants. A further object of the invention is to provide a suitable catalyst for use in such a process.

It has now been found, in the context of the present invention, that the oxidation of alcohols can also be carried out efficiently using heterogeneous, inorganically supported ruthenium catalysts in the presence of alkali metal hypochlorite or alkaline earth metal hypochlorite as oxidant. This is surprising since it is known, for example from Angew. Chem. 2002, 114, 4720-4724, that heterogeneous oxidations are generally disadvantageous because of poorer turnover numbers (TONs) and a restricted choice of substrates and, in particular, have particular advantages only in a solvent-free variant.

The present invention therefore provides a process for preparing aldehydes and ketones of the general formula (I),

(I)

where $R^1$ and $R^2$ are each, independently of one another, a hydrogen atom or a substituted or unsubstituted hydrocarbon radical which may be an alkyl group, cycloalkyl group, alkenyl group, aryl group, arylalkyl group or arylalkenyl group having, in each case, from 1 to 20 carbon atoms and may preferably be substituted by at least one substituent from the group consisting of halogen atoms, nitro, alkoxy, aryloxy, in particular phenoxy, aryl, alkyl and acyloxy, or a substituted or unsubstituted heterocyclic group which preferably has at least one heteroatom from the group consisting of oxygen, nitrogen and sulphur, or may together form a substituted or unsubstituted alkylene group which may have at least one heteroatom from the group consisting of oxygen, nitrogen and sulphur.

The process is characterized in that compounds of the formula (II),

(II)

where $R^1$ and $R^2$ are as defined above, are reacted with an alkali metal hypochlorite or alkaline earth metal hypochlorite. The alcohol as substrate can be a monoalcohol or a polyalcohol and it is possible to use a mixture of two or more of these alcohols. If the alcohol or one of the alcohols is a polyalcohol, the hydroxy groups present therein can be partly or fully oxidized to the corresponding carbonyl groups and the resulting product can be a corresponding polycarbonyl compound or a monocarbonyl or polycarbonyl compound which still contains hydroxy groups. If the alcohol or one of the alcohols is a polyalcohol, this has the general formula (II-a),

(II-a)

where $R^{1\prime}$ and $R^{2\prime}$ have the meanings given for $R^1$ and $R^2$ with the proviso that any hydroxy substituents present in $R^{1\prime}$ and $R^{2\prime}$ are completely or partly oxidized to carbonyl substituents in the target compounds of the general formula (I). Particularly preferred polyalcohols are diols such as substituted or unsubstituted ethylene glycol, 1,2- or 1,3-propanediol, 1,2-, 1,3-, 2,3- or 1,4-butanediol, 1,2- or 1,5-pentanediol, 1,2- or 1,6-hexanediol, 1,2- or 1,7-heptanediol, 1,2- or 1,8-octanediol, 1,2- or 1,10-decanediol.

In the following, the radicals $R^{1'}$ and $R^{2'}$ are, unless indicated otherwise, subsumed under $R^1$ and $R^2$.

The reaction is carried out in the presence of a heterogeneous, inorganically supported ruthenium catalyst which may be additionally doped with another transition metal TM. Such a heterogeneous, inorganically supported ruthenium catalyst is preferably represented by the general formula (IIIa) or (IIIb):

Ru/support (IIa)

Ru/TM/support (IIIb)

The scope of the invention encompasses all general or preferred radical definitions, parameters and explanations given above or in the following in any combinations with one another, i.e. between the respective ranges and preferred ranges.

For the purposes of the invention, the term aryl preferably refers, unless indicated otherwise, to carbocyclic aromatic radicals having from 6 to 24 skeletal carbon atoms or heteroaromatic radicals having from 5 to 24 skeletal carbon atoms in which no, one, two or three skeletal carbon atoms per ring, but at least one skeletal carbon atom in the total molecule, may be replaced by heteroatoms selected from the group consisting of nitrogen, sulphur and oxygen. Furthermore, the carbocyclic aromatic radicals or heteroaromatic radicals may be substituted by up to five identical or different substituents per ring selected from the group consisting of hydroxy, halogen, nitro, cyano, free or protected formyl, $C_1$-$C_{12}$-alkyl, $C_1$-$C_{12}$-haloalkyl, $C_5$-$C_{14}$-aryl, $C_6$-$C_{15}$-arylalkyl, $C_1$-$C_{12}$-alkoxy, $C_1$-$C_{12}$-alkoxycarbonyl, substituted or unsubstituted $C_1$-$C_{12}$-alkylamino or $C_1$-$C_{12}$-alkoxycarbonylamino, e.g. tert-butoxycarbonylamino (BOC-amino), carboxyl, carbonyl, $C_1$-$C_{12}$-alkylcarboxy, thiol, $C_1$-$C_{12}$-acyl, substituted or unsubstituted $C_1$-$C_{12}$-aminocarbonyl, $C_1$-$C_{12}$-acyloxycarbonyl and $C_1$-$C_{12}$-alkylthio.

The same applies to the aryl part of an arylalkyl radical.

For example, aryl is particularly preferably phenyl, naphthyl or anthracenyl which may be monosubstituted, disubstituted or trisubstituted by radicals selected independently from the group consisting of $C_1$-$C_6$-alkyl, $C_1$-$C_6$-haloalkyl, $C_5$-$C_{14}$-aryl, $C_1$-$C_6$-alkoxy, $C_1$-$C_6$-alkoxycarbonyl, halogen, hydroxy, nitro and cyano.

For the purposes of the invention, the term alkyl or alkylene or alkoxy preferably refers, unless indicated otherwise, in each case independently, to a substituted or unsubstituted straight-chain, cyclic, branched or unbranched alkyl or alkylene or alkoxy radical. The same applies to the alkylene part of an arylalkyl radical. Possible substituents for the alkyl or alkylene or alkoxy radicals are, for example, $C_1$-$C_6$-alkyl, $C_1$-$C_6$-haloalkyl, $C_5$-$C_{14}$-aryl, $C_6$-$C_{15}$-arylalkyl, $C_1$-$C_6$-alkoxy, $C_5$-$C_{14}$-aryloxy, $C_1$-$C_6$-alkoxycarbonyl, $C_1$-$C_6$-acyloxy, substituted or unsubstituted $C_1$-$C_{12}$-alkylamino or $C_1$-$C_{12}$-alkoxycarbonylamino, e.g. tert-butoxycarbonylamino (BOC-amino), carboxyl, carbonyl, $C_1$-$C_{12}$-alkylcarboxy, $C_1$-$C_{12}$-acyl, substituted or unsubstituted $C_1$-$C_{12}$-aminocarbonyl, $C_1$-$C_{12}$-acyloxycarbonyl or $C_1$-$C_{12}$-alkylthio, halogen, hydroxy, nitro or cyano.

For example, alkyl is particularly preferably substituted or unsubstituted methyl, ethyl, n-propyl, isopropyl, n-butyl, tert-butyl, n-pentyl, cyclohexyl and n-hexyl, n-heptyl, n-octyl, isooctyl, n-decyl and n-dodecyl.

For example, alkylene is preferably substituted or unsubstituted methylene, 1,1-ethylene, 1,2-ethylene, 1,1-propylene, 1,2-propylene, 1,3-propylene, 1,1-butylene, 1,2-butylene, 2,3-butylene and 1,4-butylene, 1,5-pentylene, 1,6-hexylene, 1,1-cyclohexylene, 1,4-cyclohexylene, 1,2-cyclohexylene and 1,8-octylene.

For example, alkoxy is preferably methoxy, ethoxy, isopropoxy, n-propoxy, n-butoxy, tert-butoxy and cyclohexyloxy.

Cyclic alkyl radicals may be either 3- to 7-membered homocycles or heterocycles having a total of from 3 to 20 carbon atoms, the latter preferably having 1, 2 or 3 heteroatoms. Homocyclic alkyl radicals are, for example, substituted or unsubstituted cyclopentyl or cyclohexyl; examples of heterocyclic alkyl radicals are dioxolane or phthalimide radicals.

For the purposes of the invention, the term arylalkyl preferably refers, unless indicated otherwise, in each case independently, to a straight-chain, cyclic, branched or unbranched alkyl radical which is monosubstituted or polysubstituted, particularly preferably monosubstituted, by aryl radicals as defined above. An example of an arylalkyl radical is benzyl.

For the purposes of the invention, the term haloalkyl or haloalkylene preferably refers, unless indicated otherwise, in each case independently, to a straight-chain, cyclic, branched or unbranched alkyl radical which may be monosubstituted, polysubstituted or fully substituted by halogen atoms selected independently from the group consisting of fluorine, chlorine, bromine and iodine.

For example, $C_1$-$C_8$-haloalkyl is particularly preferably trifluoromethyl, trichloromethyl, 2,2,2-trifluoroethyl, pentafluoroethyl and nonafluorobutyl.

Halogen can be fluorine, chlorine, bromine or iodine, preferably fluorine or chlorine.

Preferred compounds of the formulae (I), (II) and (III) are defined below.

In the formulae (I) and (II), $R^1$ and $R^2$ are each preferably, independently of one another, hydrogen, substituted or unsubstituted $C_1$-$C_{14}$-alkyl, substituted or unsubstituted $C_1$-$C_{20}$-alkenyl, substituted or unsubstituted $C_5$-$C_{14}$-aryl, substituted or unsubstituted $C_6$-$C_{15}$-arylalkyl, substituted or unsubstituted $C_1$-$C_{20}$-haloalkyl, substituted or unsubstituted $C_3$-$C_{20}$-cycloalkyl or substituted or unsubstituted $C_3$-$C_{20}$-cycloalkenyl.

Particular preference is here given to compounds of the formulae (I) and (II) in which $R^1$ and $R^2$ are each, independently of one another, hydrogen, substituted or unsubstituted $C_5$-$C_{14}$-aryl, substituted or unsubstituted $C_1$-$C_{20}$-alkyl or substituted or unsubstituted $C_1$-$C_{20}$-alkenyl. Very particular preference is given to compounds of the formulae (I) and (II) in which at least one of the radicals $R^1$ and $R^2$ is hydrogen. In preferred embodiments of the invention, at least one of the two radicals $R^1$ and $R^2$ is hydrogen and the other is substituted or unsubstituted $C_5$-$C_{14}$-aryl.

Particularly preferred substituents for the radicals $R^1$ and $R^2$ are methyl, ethyl, methoxy, ethoxy, fluorine, chlorine, trifluoromethyl, nitro, phenyl, phenoxy and tert-butoxycarbonylamino (BOC-amino). If the alcohols of the general formula (II) are polyalcohols of the general formula (II-a), a further preferred substituent for the radicals $R^{1'}$ and $R^{2'}$ is hydroxy and for the radicals $R^1$ and $R^2$ is carbonyl.

In the formulae (IIIa) and (IIIb), the "support" is preferably a porous inorganic solid. The support is particularly preferably a porous inorganic solid from the group consisting of activated carbon, aluminium oxide, aluminium silicate, silicon dioxide, barium sulphate, calcium carbonate, cerium dioxide, titanium dioxide and zirconium dioxide. The support is particularly preferably activated carbon, titanium dioxide and zirconium dioxide.

In the formula (IIIb), TM is preferably a transition metal and particularly preferably a transition metal from the group consisting of Cu, Mo, Mn, Fe, Co.

In a preferred embodiment, the process of the invention is carried out in the presence of water and/or one or more organic solvents such as, in particular, tertiary alcohols, aprotic polar solvents, ketones, chlorinated hydrocarbons and aromatic hydrocarbons. For the purposes of the present invention, aprotic polar solvents are solvents which at 25° C. have a dielectric constant of 5 or more and a pKa based on an aqueous reference scale at 25° C. of 20 or more. In the process of the invention, particular preference is given to water, tertiary alcohols such as, in particular, t-amyl alcohol and t-butyl alcohol and also chlorinated hydrocarbons such as 1,2-dichloroethane, methylene chloride, chloroform, chlorobenzene and dichlorobenzenes, e.g. 1,2-, 1,3- or 1,4-dichlorobenzene. In a very particularly preferred embodiment, the process is carried out in a two-phase mixture, particularly preferably in the presence of water and 1,2-dichloroethane.

The reaction is, for example, carried out by initially charging the compounds of the formula (I) and the ruthenium catalyst in a solvent and admixing them with the alkali metal hypochlorite or alkaline earth metal hypochlorite, which may be dissolved in water, and stirring the mixture for a period of up to 24 hours, preferably up to 5 hours and particularly preferably one hour. In a preferred embodiment, a solution of the oxidant is metered into the reaction mixture over a period of from 5 minutes to 24 hours, preferably 5 hours and particularly preferably 1 hour. Any additional stirring time can be, for example, up to 24 hours, preferably up to 5 hours and particularly preferably up to one hour.

The reaction can be carried out at temperatures of from −20° C. to 150° C., preferably from 0 to 80° C., particularly preferably from 0° C. to 40° C. and very particularly preferably from 15° C. to 30° C.

The pressure during the reaction is not critical and can be, for example, from 0.5 to 100 bar, preferably from 0.8 to 10 bar. Particular preference is given to ambient pressure.

As alkali metal hypochlorites and alkaline earth metal hypochlorites used as oxidant, preference is given to using sodium hypochlorite or potassium hypochlorite or calcium hypochlorite chloride, the latter, for example, in pure form or in the form of technical-grade chlorinated lime. Particular preference is given to using sodium hypochlorite. The oxidant is preferably used in an amount of from 0.5 to 10 molar equivalents based on compounds of the formula (II), particularly preferably from 1 to 5 molar equivalents and very particularly preferably from 1 to 3 molar equivalents. The oxidant is, if appropriate, advantageously used as solution and/or suspension in a solvent, particularly preferably as solution and/or suspension in water and, if appropriate, additionally at least one of the organic solvents mentioned above.

The reaction can be carried out at a neutral pH or under acidic or alkaline conditions; the addition of acids or bases may also be advantageous. The reaction is preferably carried out under alkaline conditions, particularly preferably at pH values of from 10 to 13, measured at 20° C.

The amount of inorganically supported ruthenium compound, in particular of the formula (Ma) or (IIIb), used can be selected so that the amount of ruthenium based on the alcohol of the formula (II) is from 0.0001 to 100 mol %, preferably from 0.01 to 10 mol % and particularly preferably from 0.5 to 1 mol %.

The inorganically supported ruthenium catalyst can, for example, be separated off from the reaction mixture in a simple manner by filtration or centrifugation. If appropriate, it can be washed with water and/or an organic solvent before it can be reused in the reaction.

It can be advantageous to add small amounts of suitable free-radical scavengers to the reaction. Such suitable free-radical scavengers are known to those skilled in the art; mention may be made by way of example of hydroquinone. Preference is given to using amounts of free-radical scavengers of up to 1 equivalent based on the metal content of the catalyst. Possible overoxidation to the carboxylic acid can be avoided by addition of such free-radical scavengers, but such an addition is not absolutely necessary.

Compounds of the formula (I) can be obtained with very high selectivities under mild conditions according to the invention. The work-up can be carried out in a manner known per se, e.g. by extraction with a suitable organic solvent and distillation or recrystallization of the aldehyde. Unreacted starting material can be recirculated to the process.

For the purposes of the invention, heterogeneous, inorganically supported ruthenium catalysts which may be additionally doped with one or more transition metals are used.

The ruthenium content can be from 0.01 to 20% by weight, preferably from 0.05 to 5% by weight. The content of any additional transition metal or metals present can be from 0.01 to 20% by weight, preferably from 0.1 to 5% by weight. The ruthenium content and transition metal content are based on the total mass of the catalyst. The content of the respective metal can be determined, for example, by means of ICP-OES (inductively coupled plasma—optical emission spectroscopy).

The determination can be carried out, for example, on an Optima 3000 XL instrument from Perkin Elmer and an EA 1110 instrument from CE Instruments.

In the catalysts, in particular those of the formulae (IIIa) and (IIIb), ruthenium can be present in the formal oxidation states 0 to +VII, with the oxidation states 0 and +III being preferred and the oxidation state +III being particularly preferred. The oxidation state of ruthenium can, for example, be determined by means of XPS (binding energy of the [$Ru3d_{5/2}$ level]). The XPS measurements can, for example, be carried out on a VG ESCALAB 220 i XL using $Alk_\alpha$ radiation (1486.8 eV). Such instruments are known to those skilled in the art. To determine the electron binding energy, the C1s signal at 284.4 eV is selected as reference point.

In preferred embodiments of the process of the invention, the diameter of the ruthenium particles, which can be determined by transmission electron microscopy (TEM), on the support is 20 nm or less in the catalysts of the formulae (IIIa) and (IIIb). In particularly preferred embodiments of the process of the invention, the diameter of the ruthenium particles on the support is 2 nm or less. The TEM measurements can, for example, be carried out using a Phillips CM-20 instrument at an acceleration power of 200 kW.

The properties such as the BET surface area of the materials used as inorganic supports are not subject to any restrictions. As titanium dioxides, it is possible to use, for example, P25 (BET surface area: 50 $m^2/g \pm 15\ m^2/g$) from Degussa or $TiO_2$ from Kronos (BET surface area: 307 $m^2/g$). As zirconium dioxide, it is possible to use, for example, $Zr(OH)_4$ MELCAT XZ0631/01 from MEL Chemicals (BET surface area: 459 $m^2/g$). The determination of the BET surface areas can be carried out, for example, by means of an ASAP 2000-Mg as adsorption system at 77° C. Such an instrument is known to those skilled in the art.

The preparation of the inorganically supported ruthenium catalysts, which may be doped with one or more transition metals, of the general formula (IIIa) or (IIIb) can, for example, be carried out by wet-chemical impregnation using a method based on that of Mizuno et al., *Angew. Chem.* 2002, 114, 4720, by placing a particular amount of a ruthenium(III) precursor, for example ruthenium(III) chloride, and, if appropriate, a particular amount of one or more transition metal compound(s), for example iron(II) sulphate or cobalt(II) chloride, together with a suitable solvent, for example water, in a reaction vessel and adding the support while stirring. The solid is then separated off from the liquid phase, for example by filtration or centrifugation. The solid is, if appropriate, washed with water and dried. The solid is then suspended in water and the mixture obtained is made alkaline, for example by means of dilute sodium hydroxide solution. After stirring for a number of hours, the solid is separated off from the liquid phase, for example by filtration or centrifugation. The solid is, if appropriate, washed with water and dried.

In a modified wet-chemical method of preparation, inorganically supported ruthenium catalysts of the formula (IIIb) which are doped with one or more transition metals can also be prepared by placing the transition metal compound(s) together with water in a reaction vessel and adding an inorganically supported ruthenium catalyst while stirring. The further procedure involving separation of solid, washing, drying, suspension in water, setting of an alkali pH, solid separation, washing and drying are carried out as described in the preceding section.

The preparation of the inorganically supported ruthenium catalysts, which may be doped with one or more transition metals, of the general formula (Ma) or (Mb) can also be carried out by the MPECVD (microwave plasma-enhanced chemical vapor deposition) method, for example in an Ilmplac 1200 microwave plasma instrument. This variant can, for example, be carried out by placing a particular amount of a ruthenium(III) precursor, for example ruthenium(III) acetylacetonate, and, if appropriate, a particular amount of one or more transition metal compound(s), for example cobalt(II) acetylacetonate, together with a particular amount of the support in the MPECVD instrument. The deposition of the ruthenium species and, if appropriate, the further transition metal species on the support can, for example, be carried out in a low-pressure oxygen plasma, and a subsequent treatment with a hydrogen plasma can be carried out if appropriate.

Examples of catalysts of the formulae (IIIa) and (IIIb) are the compounds of the formulae (III-1) to (III-12). In the abbreviations for the supported catalysts, W denotes the wet-chemical method of preparation and P denotes the plasma-chemical method of preparation, and the number after the respective metal which is applied to the support indicates the loading with this metal in percent by weight, based on the total mass of the catalyst. The name/number in brackets is the commercial designation of the support material.

| Numbering | Catalyst |
|---|---|
| III-1 | W—Ru 0.83/$TiO_2$ (Kronos) |
| III-2 | W—Ru 0.50/$TiO_2$ (P25) |
| III-3 | W—Ru 1.36/$TiO_2$ (P25) |
| III-4 | W—Ru 1.57/$TiO_2$ (P25) |
| III-5 | W—Ru 1.9/$TiO_2$ (P25) |
| III-6 | W—Ru 2.13/$ZrO_2$ |
| III-7 | W—Ru 1.85/Cu 0.18/$TiO_2$ (P25) |
| III-8 | W—Ru 1.1/Fe 0.30/$TiO_2$ (P25) |
| III-9 | W—Ru 0.45/Co 0.36/$TiO_2$ (P25) |

-continued

| Numbering | Catalyst |
|---|---|
| III-10 | W—Ru 0.44/Mn 0.35/$TiO_2$ (P25) |
| III-11 | P—Ru 0.2/$TiO_2$ (P25) |
| III-12 | P—Ru 0.34/$TiO_2$ (P25) |
| III-13 | P—Ru 1.57/$TiO_2$ (P25) |
| III-14 | P—Ru 0.32/Co 0.51/$TiO_2$ (P25) |

Furthermore, commercially available supported ruthenium/activated carbon catalysts were used:

III-15: H 101 R/W (5% Ru/C; Degussa)

III-16: Escat 440 (5% Ru/C; Engelhard)

III-17: K-0402 (5% Ru/C; Heraeus)

Furthermore, a commercially available supported ruthenium/$Al_2O_3$ catalyst was used:

III-18: K-0453 (5% Ru/$Al_2O_3$; Heraeus)

The present invention further provides inorganically supported ruthenium catalysts, preferably catalysts of the general formula (IIIa) or (IIIb), in which the diameter of the ruthenium particles on the support is 20 nm or less, preferably 5 nm or less, particularly preferably 2 nm or less. The diameters of the ruthenium particles on the support can be determined by transmission electron microscopy (TEM). The inorganically supported ruthenium catalysts of the invention are preferably ones in which titanium dioxide or zirconium dioxide is used as support.

Furthermore, the abovementioned definitions and preferred ranges for the inorganically supported ruthenium catalysts used according to the invention, in particular those of the general formula (IIIa) and (IIIb), and the information on their preparation apply to the catalysts of the invention.

The catalysts of the invention are particularly useful for the catalytic oxidation of alcohols to aldehydes or ketones, preferably for use in the above-described process of the invention.

The compounds of the formula (I) which can be prepared according to the invention are particularly useful for preparing pharmaceutical or agrochemical active ingredients, polymers, specialty chemicals or intermediates thereof.

In the process of the invention, the oxidation of primary and secondary alcohols proceeds under very mild conditions with high chemoselectivity and gives the corresponding aldehydes and ketones in very high selectivities. Particular mention may be made of the very small amounts of inorganically supported ruthenium catalyst required, which can be separated off from the reaction mixture in a simple manner and be reused for the reaction. At the same time, the ability to use the inexpensive alkali metal hypochlorites or alkaline earth metal hypochlorites, in particular sodium hypochlorite (chlorine bleach), as oxidant is a particular advantage.

The following examples illustrate the invention and are not to be regarded as a restriction.

EXAMPLES

The binding energy of the [$Ru3d_{5/2}$ level]) was determined by means of XPS measurements on a VG ESCALAB 2201 XL using $AlK_\alpha$ radiation (1486.6 eV). The C1s signal at 284.4 eV was selected as reference point for the determination.

The diameter of the ruthenium particles was determined by means of TEM measurements using a Philips CM-20 instrument at an acceleration power of 200 kW.

The content of the respective metal (metal loading) was determined by means of ICP-OES on an Optima 3000 XL instrument from Perkin Elmer or an EA 1110 instrument from CE Instruments.

The determination of the BET surface areas was carried out by means of an ASAP 2000-Mg as adsorption system at 77° C.

Example 1

General Method of Preparation for the Catalysts III-1 to III-8

$RuCl_3$ or $RuCl_3.xH_2O$ were, if appropriate together with a transition metal compound, dissolved in a particular amount of water and the support was added while stirring. The suspension was stirred for 15 minutes and then centrifuged at 7000 rpm. The supernatant liquid was decanted off, the solid residue was washed with water and centrifuged again. This washing procedure was repeated twice more, so that a colourless washing liquor was obtained. The solid was dried at room temperature under reduced pressure for 24-48 hours and then ground in a mortar. The solid was then suspended in 90-180 ml of water and the mixture was brought to a pH of 13.2 by means of aqueous sodium hydroxide solution (1 molar). After stirring for 24 hours, the mixture was centrifuged and the solid residue was washed three times with water. The solid was dried at room temperature for 24 hours and then at 50° C. under reduced pressure for 4 hours.

Catalyst III-1: 103 mg of $RuCl_3$; 2 g of $TiO_2$ (Kronos); 60 ml of water; yield 1.87 g.

Catalyst III-2: 152 mg of $RuCl_3.xH_2O$; 10 g of $TiO_2$ (P25); 180 ml of water; yield 8.12 g.

Catalyst III-3: 304 mg of $RuCl_3.xH_2O$; 10 g of $TiO_2$ (P25); 180 ml of water; yield 7.99 g.

Catalyst III-4: 516 mg of $RuCl_3$; 10 g of $TiO_2$ (P25); 180 ml of water; yield 8.20 g.

Catalyst III-5: 516 mg of $RuCl_3$; 10 g of $TiO_2$ (P25); 300 ml of water; yield 7.33 g.

Catalyst III-6: 310 mg of $RuCl_3$; 6 g of $ZrO_2$; 180 ml of water; yield 4.87 g.

Catalyst III-7: 103 mg of $RuCl_3$; 10 mg of CuCl; 2 g of $TiO_2$ (P25); 60 ml of water; yield 1.85 g.

Catalyst III-8: 103 mg of $RuCl_3$; 32 mg of $FeSO_4.xH_2O$; 2 g of $TiO_2$ (P25); 60 ml of water; yield 1.49 g.

TABLE 1

Characterization of the catalysts III-1 to III-8

| Numbering | Metal loading [% by weight] | Diameter of the Ru particles [nm] | BET surface area [m$^2$/g] | Binding energy [eV] |
|---|---|---|---|---|
| III-1 | Ru 0.83 | ≦1 | 253.8 | [Ru3d$_{5/2}$] 282.5 |
| III-2 | Ru 0.50 | ≦2 | 55.4 | [Ru3d$_{5/2}$] 282.1 |
| III-3 | Ru 1.36 | n.d. | 53.6 | n.d. |
| III-4 | Ru 1.57 | 1-5 | 57.9 | [Ru3d$_{5/2}$] 282.1 |
| III-5 | Ru 1.90 | ≦1-2 | 62.8 | [Ru3d$_{5/2}$] 281.5 |
| III-6 | Ru 2.13 | ≦2 | 433.5 | [Ru3d$_{5/2}$] 281.8 |
| III-7 | Ru 1.85; Cu 0.18 | n.d. | 57.2 | [Ru3d$_{5/2}$] 281.8 [Cu2p$_{3/2}$] 929.7 |
| III-8 | Ru 1.1; Fe 0.30 | n.d. | 55.0 | n.d. | n.d. = not determined

The binding energies determined are in the characteristic range for ruthenium in the oxidation state +III.

Example 2

Preparation of the Catalysts III-9 and III-10

A particular amount of a cobalt compound or a manganese compound was dissolved in water and 4 g of the catalyst III-2 [W—Ru 0.50/$TiO_2$ (P25)] were added while stirring. The suspension was stirred for 24 hours and then centrifuged at 7000 rpm. The supernatant liquid was decanted off, and the solid residue was washed with water and centrifuged again. This washing procedure was repeated twice more. The solid was dried at room temperature under reduced pressure for 25 hours and then ground in a mortar. The solid was then suspended in 90 ml of water and the mixture was brought to a pH of 13.2 by means of aqueous sodium hydroxide solution (1M). After stirring for 24 hours, the mixture was centrifuged and the solid residue was washed three times with water. The solid was dried at room temperature under reduced pressure for 24 hours.

Catalyst III-9: 292 mg of $Co(OAc)_2.4H_2O$; yield 3.47 g.

Catalyst III-10: 288 mg of $Mn(OAc)_2.4H_2O$; yield 3.34 g.

TABLE 2

Characterization of the catalysts III-9 and III-10

| Numbering | Metal loading [% by weight] | Diameter of the Ru particles [nm] | BET surface area [m$^2$/g] | Binding energy [eV] |
|---|---|---|---|---|
| III-9 | Ru 0.45; Co 0.36 | ≦2 | 52.9 | [Ru3d$_{5/2}$] 282.1 [Co2p$_{3/2}$] 780.5 |
| III-10 | Ru 0.44; Mn 0.35 | ≦2 | 58.5 | [Ru3d$_{5/2}$] 282.2 [Mn2p$_{3/2}$] 640.9 | n.d. = not determined

The binding energies determined are in the characteristic range for ruthenium in the oxidation state +III.

Example 3

Plasma-Chemical Preparation of the Catalysts III-11 to III-14

A particular amount of ruthenium(III) acetylacetonate and, in the case of the catalyst III-14, also a particular amount of cobalt(II) acetylacetonate were placed together with 3 g of titanium dioxide (P25) in an MPECVD instrument (Ilmplac 1200 microwave plasma instrument). A vacuum of 10 Pa was subsequently set. The plasma was ignited at an oxygen flow of 300 cm$^3$/min and a microwave power of 300 W. Catalyst III-13 was additionally treated with a hydrogen plasma.

Catalyst III-11: 84 mg of Ru(III) acetylacetonate

Catalyst III-12: 167 mg of Ru(III) acetylacetonate

Catalyst III-13: 240 mg of Ru(III) acetylacetonate

Catalyst III-14: 120 mg of Ru(III) acetylacetonate; 77 mg of cobalt(II) acetylacetonate

TABLE 3

Characterization of the catalysts III-11 to III-14

| Numbering | Metal loading [% by weight] | Diameter of the Ru particles [nm] | BET surface area [m²/g] | Binding energy [eV] |
|---|---|---|---|---|
| III-11 | Ru 0.2 | ≦5 | 60.2 | [Ru3d$_{5/2}$] 280.6 |
| III-12 | Ru 0.34 | 1-10 | 59.4 | [Ru3d$_{5/2}$] 280.3 |
| III-13 | Ru 1.57 | 1.5-10 | 58.7 | [Ru3d$_{5/2}$] 280.7 |
| III-14 | Ru 0.32; Co 0.51 | 1-10 | 59.6 | [Ru3d$_{5/2}$] 282.3 |
|  |  |  |  | [Co2p$_{3/2}$] 780.5 | n.d. = not determined

The binding energies determined for the catalysts III-11, III-12 and III-13 are slightly above the characteristic range for ruthenium in the oxidation state 0, from which it can be deduced that the major part of the ruthenium in the catalysts III-11, 111-12 and III-13 is present in the form of metallic ruthenium. The binding energy determined for the catalyst III-14 is increased by the presence of the promoter metal Co, so that, taking this increase into account, the value likewise indicates ruthenium in the oxidation state 0, i.e. the major part of the ruthenium is present as metallic ruthenium.

Example 4

General Experimental Description for the Oxidation of Alcohols by Means of Sodium Hypochlorite 1 mmol of the respective alcohol together with 7 ml of the respective solvent were placed in a reaction flask and the catalyst was added while stirring. Aqueous sodium hypochlorite solution (from Sigma-Aldrich, 10-13% of active chlorine) was used as oxidant and was metered into the reaction mixture over a period of 60 minutes by means of a syringe pump. The mixture was stirred further for a particular time. The organic components were subsequently separated off by triple extraction with 1,2-dichloroethane. The combined organic phases were analysed by gas chromatography. Gas chromatography was carried out on a Hewlett Packard HP 5890 instrument equipped with an HP5 column and a mass-selective detector (HP 5971 A). Diethylene glycol di-n-butyl ether was used as internal standard. To detect any carboxylic acids formed, trimethylsulphonium hydroxide was added to the analytical sample prior to the measurement.

All the experiments listed in the following tables were carried out according to the general experimental description (Example 4).

TABLE 4

Oxidation of benzyl alcohol using various catalysts, solvents and amounts of NaOCl.

| Catalyst | Ru [mmol] | Solvent | NaOCl [mmol] | Conversion [%] | Selectivity to aldehyde [%] | Selectivity to benzoic acid [%] |
|---|---|---|---|---|---|---|
| III-5 | 0.01 | 3.5 ml of H$_2$O/ 3.5 ml of t-BuOH | 1.1 | 44 | >99 | 0 |
| III-5 | 0.01 | 3.5 ml of H$_2$O/ 3.5 ml of t-BuOH | 1.1 | 66 | >99 | 0 |
| III-5 | 0.01 | 7 ml of t-BuOH | 1.1 | 42 | 90 | 9 |
| III-5 | 0.01 | 3.5 ml of H$_2$O/ 3.5 ml of DCE | 1.1 | 83 | >99 | 0 |
| III-5 | 0.01 | 3.5 ml of H$_2$O/ 3.5 ml of DCE | 1.1$^a$ | 76 | 96 | 3 |
| III-5 | 0.005 | 3.5 ml of H$_2$O/ 3.5 ml of DCE | 1.1$^a$ | 77 | >99 | 0 |
| III-1 | 0.01 | 3.5 ml of H$_2$O/ 3.5 ml of DCE | 1.1 | 74 | 98 | 1 |
| III-6 | 0.01 | 3.5 ml of H$_2$O/ 3.5 ml of DCE | 1.1 | 77 | 98 | 1 |
| III-12 | 0.005 | 3.5 ml of H$_2$O/ 3.5 ml of DCE | 1.1 | 47 | 50 | 49 |
| III-7 | 0.01 | 3.5 ml of H$_2$O/ 3.5 ml of DCE | 1.1 | 75 | 97 | 3 |
| III-8 | 0.01 | 3.5 ml of H$_2$O/ 3.5 ml of DCE | 1.1 | 72 | 97 | 3 |
| III-9 | 0.005 | 3.5 ml of H$_2$O/ 3.5 ml of DCE | 1.1 | 38 | 50 | 50 |
| III-10 | 0.005 | 3.5 ml of H$_2$O/ 3.5 ml of DCE | 1.1 | 85 | 87 | 13 |
| III-5 | 0.01 | 3.5 ml of H$_2$O/ 3.5 ml of DCE | 1.3 | 85 | 95 | 5 |
| III-5 | 0.01 | 3.5 ml of H$_2$O/ 3.5 ml of DCE | 1.5 | 100 | 86 | 14 |
| III-5 | 0.01 | 3.5 ml of H$_2$O/ 3.5 ml of DCE | 2 | 100 | 74 | 26 |
| III-1 | 0.01 | 3.5 ml of H$_2$O/ 3.5 ml of DCE | 1.5 | 80 | 97 | 2 |
| III-6 | 0.01 | 3.5 ml of H$_2$O/ 3.5 ml of DCE | 1.5 | 90 | 98 | 2 |
| III-7 | 0.01 | 3.5 ml of H$_2$O/ 3.5 ml of DCE | 1.5 | 97 | 94 | 6 |

TABLE 4-continued

Oxidation of benzyl alcohol using various catalysts, solvents and amounts of NaOCl.

| Catalyst | Ru [mmol] | Solvent | NaOCl [mmol] | Conversion [%] | Selectivity to aldehyde [%] | Selectivity to benzoic acid [%] |
|---|---|---|---|---|---|---|
| III-15 | 0.01 | 3.5 ml of $H_2O$/ 3.5 ml of DCE | 1.1 | 55 | 99 | 1 |
| III-16 | 0.01 | 3.5 ml of $H_2O$/ 3.5 ml of DCE | 1.1 | 57 | 96 | 3 |
| III-17 | 0.01 | 3.5 ml of $H_2O$/ 3.5 ml of DCE | 1.1 | 66 | 99 | 1 |
| III-18 | 0.005 | 7 ml of t-BuOH | 1.1 | 19 | 99 | 0 |

Reaction conditions: 1 mmol of benzyl alcohol, room temperature, further stirring time: 10 min;
$^a$Further stirring time: 130 min,
DCE = 1,2-dichloroethane.

TABLE 5

Oxidation of benzyl alcohol at various pH values.

| Catalyst | Ru [mmol] | Solvent | pH | Conversion [%] | Selectivity to aldehyde [%] | Selectivity to benzoic acid [%] |
|---|---|---|---|---|---|---|
| III-5 | 0.01 | 3.5 ml of buffer/ 3.5 ml of DCE | 9 | 65 | 95 | 6 |
| III-5 | 0.01 | 3.5 ml of buffer/ 3.5 ml of DCE | 10 | 65 | 96 | 5 |
| III-5 | 0.01 | 3.5 ml of buffer/ 3.5 ml of DCE | 11 | 73 | 95 | 5 |
| III-5 | 0.01 | 3.5 ml of buffer/ 3.5 ml of DCE | 12 | 67 | 96 | 4 |
| III-5 | 0.01 | 3.5 ml of buffer/ 3.5 ml of DCE | 13 | 64 | 95 | 6 |

Reaction conditions: 0.005 mmol of Ru, 1 mmol of benzyl alcohol, room temperature, further stirring time: 10 min;
DCE = 1,2-dichloroethane.

TABLE 6

Oxidation of various alcohols using catalyst III-5 [W—Ru 1.9/$TiO_2$ (P25)].

| Alcohol | Conversion [%] | Selectivity to aldehyde or ketone [%] | Selectivity to carboxylic acid [%] |
|---|---|---|---|
| 2-methoxybenzyl alcohol (CH$_2$OH, OCH$_3$) | 62 | 98 | 2 |
| 4-nitrobenzyl alcohol (CH$_2$OH, O$_2$N) | 100 | 99 | 1 |
| 2,4-dichlorobenzyl alcohol (Cl, Cl, CH$_2$OH) | 62 | 80 | 20 |
| 4-trifluoromethylbenzyl alcohol (F$_3$C, CH$_2$OH) | 55 | 91 | 9 |
| 4-fluorobenzyl alcohol (F, CH$_2$OH) | 67 | 99 | 1 |
| 3-nitrobenzyl alcohol (O$_2$N, CH$_2$OH) | 35 | 96 | 3 |
| 3,5-bis(trifluoromethyl)benzyl alcohol (F$_3$C, CH$_2$OH, CF$_3$) | 58 | >99 | 0 |

TABLE 6-continued

Oxidation of various alcohols using catalyst III-5
[W—Ru 1.9/TiO$_2$ (P25)].

| Alcohol | Conversion [%] | Selectivity to aldehyde or ketone [%] | Selectivity to carboxylic acid [%] |
|---|---|---|---|
| 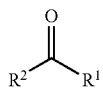 | 73 | 98 | 1 |
| 1-octanol | 36 | 77 | 22 |
| trans-cinnamyl alcohol | 20 | 37 | 0 |
| N—BOC-D-leucinol | 2 | >99 | 0 |
| Cyclohexanol | 33 | 87 | 0 |

Reaction conditions: 0.005 mmol of catalyst III-5; 1 mmol of alcohol, 3.5 ml of H$_2$O/3.5 ml of 1,2-dichloroethane, room temperature, further stirring time: 10 min.

The invention claimed is:

1. A process for preparing aldehydes of the general formula (I),

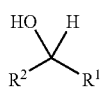 (I)

where

R$^1$ hydrogen atom and R$^2$ is benzyl, phenyl, naphthyl or anthracenyl which may be monsubstituted, disubstituted or trisubstituted by radicals selected from the group consisting of C$_1$-C$_6$-alkyl, C$_1$-C$_6$-haloalkyl, C$_5$-C$_{14}$-aryl, C$_1$-C$_6$-alkoxy, C$_1$-C$_6$-alkoxycarbonyl, halogen, hydroxyl, nitro, and cyano comprising reacting one or more compound(s) of the general formula (II), $$\underset{R^2 \quad R^1}{\overset{HO \quad H}{\diagdown \diagup}}$$ (II)

where R$^1$ and R$^2$ are as defined above, with an alkali metal hypochlorite or an alkaline earth metal hypochlorite in the presence of a ruthenium catalyst wherein the ruthenium catalyst comprises the general formula (IIIa) or (IIIb)

Ru/support (IIIa)

Ru/TM/support (IIIb), where

TM is a transition metal and support is an inorganic support material, comprising a porous inorganic solid selected from the group consisting of activated carbon, titanium dioxide and zirconium dioxide.

2. The process according to claim 1, wherein the reaction is carried out in the presence of water and/or one or more organic solvents.

3. The process according to claim 1, wherein the alkali metal hypochlorite and/or alkaline earth metal hypochlorite comprise sodium hypochlorite, potassium hypochlorite, or calcium hypochlorite chloride.

4. The process according to claim 1, wherein the alkali metal hypochlorite and/or alkaline earth metal hypochlorite is present in an amount ranging from 0.5 to 10 molar equivalents based on the molar amount of the compounds of the formula (II).

5. A method for the catalytic oxidation of alcohols to aldehydes according to claim 1 wherein Ru comprises particles where the diameter of the ruthenium particles on the support is 20 nm or less.

6. The process according to claim 2 wherein the organic solvent comprises tertiary alcohols, aprotic polar solvents, ketones, chlorinated hydrocarbons and/or aromatic hydrocarbons.

7. The process of claim 1 wherein the ruthenium catalyst comprises a second transition metal.

8. The process of claim 7 wherein the second transition metal is selected from the group consisting of Cu, Mo, Mn, Fe, and Co.

9. The process according to claim 1 wherein R$^2$ is phenyl which may be monsubstituted, disubstituted, or trisubstituted by radicals selected from the group consisting of C$_1$-C$_6$-alkyl, C$_1$-C$_6$-haloalkyl, halogen, nitro, and C$_1$-C$_6$-alkoxy.

* * * * *